US009533176B2

(12) United States Patent
Ostrovsky et al.

(10) Patent No.: US 9,533,176 B2
(45) **Date of Patent: *Jan. 3, 2017**

(54) DEVICE AND METHOD FOR DETECTING AND TREATING LESIONS

(75) Inventors: Isaac Ostrovsky, Wellesley, MA (US); Jon T. McIntyre, Newton, MA (US); Ty Fairneny, Hopkinton, MA (US); Victor Shukhat, Canton, MA (US); Michael Madden, Princeton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1871 days.

This patent is subject to a terminal disclaimer.

(21) Appl. No.: 12/249,134

(22) Filed: Oct. 10, 2008

(65) Prior Publication Data

US 2009/0259150 A1 Oct. 15, 2009

Related U.S. Application Data

(60) Provisional application No. 60/979,306, filed on Oct. 11, 2007.

(51) Int. Cl.

| | |
|---|---|
| ***A61B 5/05*** | (2006.01) |
| ***A61N 7/02*** | (2006.01) |
| *A61B 5/00* | (2006.01) |
| *A61B 17/00* | (2006.01) |
| *A61B 18/00* | (2006.01) |

(52) U.S. Cl.

CPC ............. *A61N 7/022* (2013.01); *A61B 5/4325* (2013.01); *A61B 5/0084* (2013.01); *A61B 2017/00061* (2013.01); *A61B 2018/00023* (2013.01); *A61B 2090/306* (2016.02)

(58) Field of Classification Search

USPC ........ 601/2–3; 600/407, 466, 459, 467, 471, 600/473, 476, 477, 478, 127, 178, 181, 182, 600/427; 606/27

See application file for complete search history.

(56) References Cited

U.S. PATENT DOCUMENTS

| | | | |
|---|---|---|---|
| 4,266,549 A | | 5/1981 | Kimura |
| 4,336,809 A | | 6/1982 | Clark |
| 5,078,150 A | | 1/1992 | Hara et al. |
| 5,511,424 A | * | 4/1996 | MacLauchlan et al. ........ 73/609 |
| 5,895,356 A | * | 4/1999 | Andrus et al. ................ 600/439 |
| 6,206,842 B1 | * | 3/2001 | Tu et al. ........................... 601/2 |
| 6,258,576 B1 | | 7/2001 | Richards-Kortum et al. |
| 6,618,620 B1 | | 9/2003 | Freundlich et al. |

(Continued)

FOREIGN PATENT DOCUMENTS

| | | |
|---|---|---|
| EP | 0 774 276 | 5/1997 |

OTHER PUBLICATIONS

Gheorghe, C. , Narrow-Band Imaging Endoscopy for Diagnosis of Malignant and Premalignant Gastrointestinal Lesions, J. Gastrointest. Liver Dis., vol. 15, No. 1, 77-82 (Mar. 2006).*

(Continued)

*Primary Examiner* — Rajeev Siripurapu

(74) *Attorney, Agent, or Firm* — Bookoff McAndrews, PLLC

(57) ABSTRACT

A device for treating tissue comprises an enlongate probe and a light delivery unit illuminating a target area with light within a first wavelength band selected to enhance identification of target tissue in combination with an ultrasound crystal mounted at a distal end of the probe, the crystal being stimulated to treat target tissue identified using the light delivery unit.

24 Claims, 3 Drawing Sheets

(56) References Cited

U.S. PATENT DOCUMENTS

| | | | | |
|---|---|---|---|---|
| 6,671,540 | B1 | 12/2003 | Hochman | |
| 2002/0192221 | A1 | 12/2002 | Roach | |
| 2003/0130575 | A1 | 7/2003 | Desai | |
| 2004/0059397 | A1* | 3/2004 | Sinofsky et al. | 607/88 |
| 2005/0085726 | A1* | 4/2005 | Lacoste et al. | 600/439 |
| 2005/0203399 | A1 | 9/2005 | Vaezy et al. | |
| 2006/0058622 | A1 | 3/2006 | Tearney et al. | |
| 2006/0084891 | A1* | 4/2006 | Barthe et al. | 601/2 |
| 2006/0100615 | A1 | 5/2006 | McIntyre et al. | |
| 2007/0232871 | A1 | 10/2007 | Sinofsky et al. | |

OTHER PUBLICATIONS www.thefreedictionary.com/chamber (Jul. 16, 2013).*

Demco, "Laparoscopic Spectral Analysis of Endometriosis," Journal of American Assoc Gynecol Laparosc, vol. 11, No. 2, May 11, 2004, Abstract, 1 sheet.

* cited by examiner

DEVICE AND METHOD FOR DETECTING AND TREATING LESIONS

PRIORITY CLAIM

This application claims the priority to the U.S. Provisional Application Ser. No. 60/979,306, entitled "Device and Method for Detecting and Treating Lesions" filed Oct. 11, 2007. The specification of the above-identified application is incorporated herewith by reference.

BACKGROUND

Lesions and abnormal tissue growths within organs and body lumens are often difficult to treat because they are not easily accessed. For example, endometriosis lesions are difficult to access for identification and treatment.

Laparoscopic procedures allow minimally invasive access to the interiors of many organs and body lumens. However, difficulties in accessing certain target areas remain and thus, therapies often do not completely treat conditions in these areas.

SUMMARY OF THE INVENTION

In one aspect, the present invention is directed to a device for treating tissue comprising an elongate probe and a light delivery unit illuminating a target area with light within a first wavelength band selected to enhance identification of target tissue in combination with an ultrasound crystal mounted at a distal end of the probe, the crystal being stimulated to treat target tissue identified using the light delivery unit.

DETAILED DESCRIPTION

Figure 1:
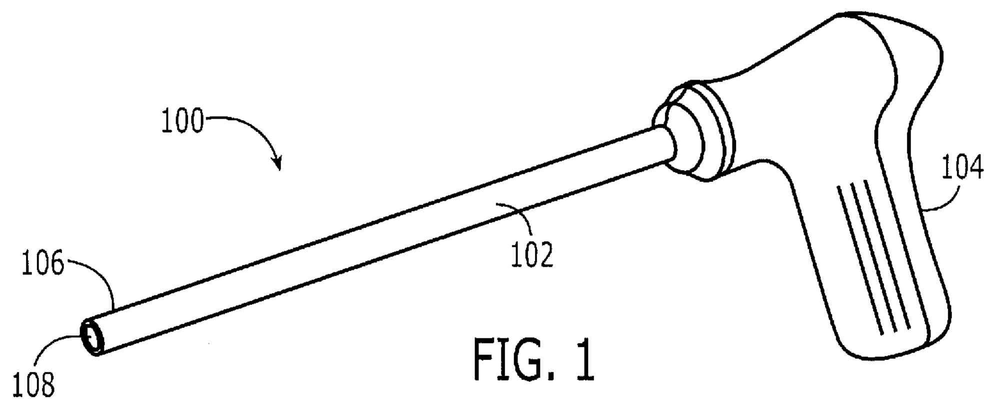
FIG. 1 is a perspective view showing an embodiment of an endometriosis treatment device according to the invention.

The present invention may be further understood with reference to the following description and to the appended drawings, wherein like elements are referred to with the same reference numerals. The present invention relates to devices for diagnosing and treating tissue within hollow organs and body lumens.

The embodiments of the present invention provide a device for detecting and treating tissue within a hollow organ or body lumen. The device may be incorporated into a laparoscopic instrument, for example to be used in the treatment of endometriosis lesions, or may be included in an endoscope for GI/esophageal applications, a bronchoscope, a cystoscope, colonoscope, ureteroscope, an hysteroscope or other minimally invasive surgical device. Different embodiments may be included in hand held probes for superficial applications, such as the treatment of skin conditions and varicose veins.

The surgical instrument according to the invention illuminates target tissue with light of desired wavelengths which may, for example, be selected to facilitate the identification of abnormal tissue. Identification may be made by the user using a vision tool or by an automated system as will be described in greater detail below. Furthermore, the wavelength of the light may be fixed or variable as dictated by the requirements of a particular procedure. As would be understood by those skilled in the art, the therapeutic functions provided by the surgical instrument may comprise excision, ablation or other treatment of tissue using a variety of technologies. Ultrasonic, radio-frequency, laser and microwave ablation may be used, as well as cryogenic ablation or surgical removal, depending on the requirements of the procedure. In one exemplary embodiment, the surgical instrument according to the invention may be used to treat endometriosis lesions which have proven difficult to accurately locate using conventional systems.

The exemplary embodiments of the surgical instrument according to this embodiment of the invention improve the identification of target (i.e., lesion) tissue by providing a blue light in the frequency range of about 440 nm instead or in addition to a conventional white light to illuminate the general treatment area. Under the blue light, the lesion tissue, even the tissue of clear microscopic lesions, stands out from surrounding "normal" tissue facilitating its accurate location.

The exemplary surgical instrument also comprises a treatment component for treating lesions that have been identified. For example, an ultrasound crystal may be provided at the distal end of the device to ablate lesions or other target tissue at selected depths, rapidly and safely. For example, a single crystal ultrasound probe may be used to deliver energy of about 10 MHz to about 20 MHz. The acoustic energy is absorbed by the tissue which is heated thereby to temperatures of 100° C. or more although such high temperatures may not be necessary to fully ablate the lesions.

As shown in FIG. 1, an exemplary handheld probe 100 for the detection and treatment of endometriosis lesions comprises an elongated shaft 102 with a distal end 106 that is inserted into the body. A handle 104 connected to the proximal end of the elongated shaft 102 facilitates manipulation of the probe 100 to access desired locations. The distal end 106 comprises diagnostic and treatment apparatus as will be further described below. For laparoscopic applications, the elongated shaft 102 is sized to fit into a trocar, for example, a 10 mm trocar.

Figure 2:
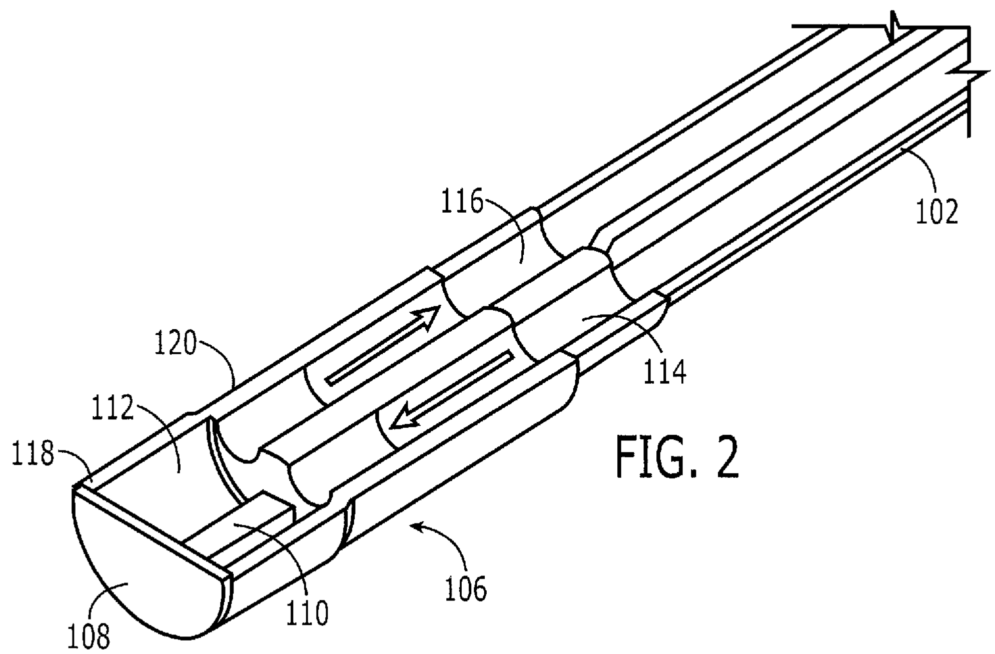
FIG. 2 is an exploded view showing the distal tip with an ultrasound crystal of the endometriosis treatment device shown in FIG. 1.

The distal end 106 of the elongated shaft 102 is shown in greater detail in FIG. 2, with emphasis on an assembly of an ultrasound crystal 108 into the probe 100. The ultrasound crystal 108 is fixed in place by a crystal holder 118 of a housing 120 with an electrical conductor 110 powering the crystal 108 comprising, for example, positive and negative leads. As would be understood by those skilled in the art, when excited by electric power, the ultrasound crystal 108 vibrates to generate ultrasound energy between, for example, about 3 MHz to about 20 MHz.

The exemplary crystal 108 is cooled to prevent overheating, and to prevent tissue from adhering to a distal face thereof during the procedure. For example, a space 112 defined by the crystal housing 120 at the distal tip 106 proximal to the crystal 108 forms a cooling chamber. To maintain the temperature of the ultrasound crystal 108 within desired limits, water or another cooling fluid may be supplied to the space 112 via supply and return channels 114, 116, respectively, which extend through the elongated shaft 102 to a pump or similar device in the handle 104 or external to the device which motivates the fluid.

Figure 3:
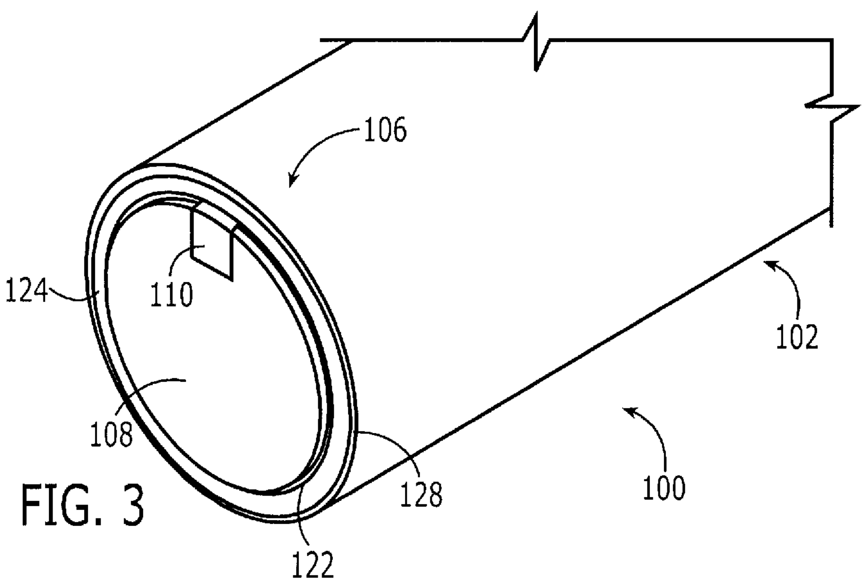
FIG. 3 is a detail view of the distal tip with optical fibers of the endometriosis treatment device shown in FIG. 1.
Figure 4:
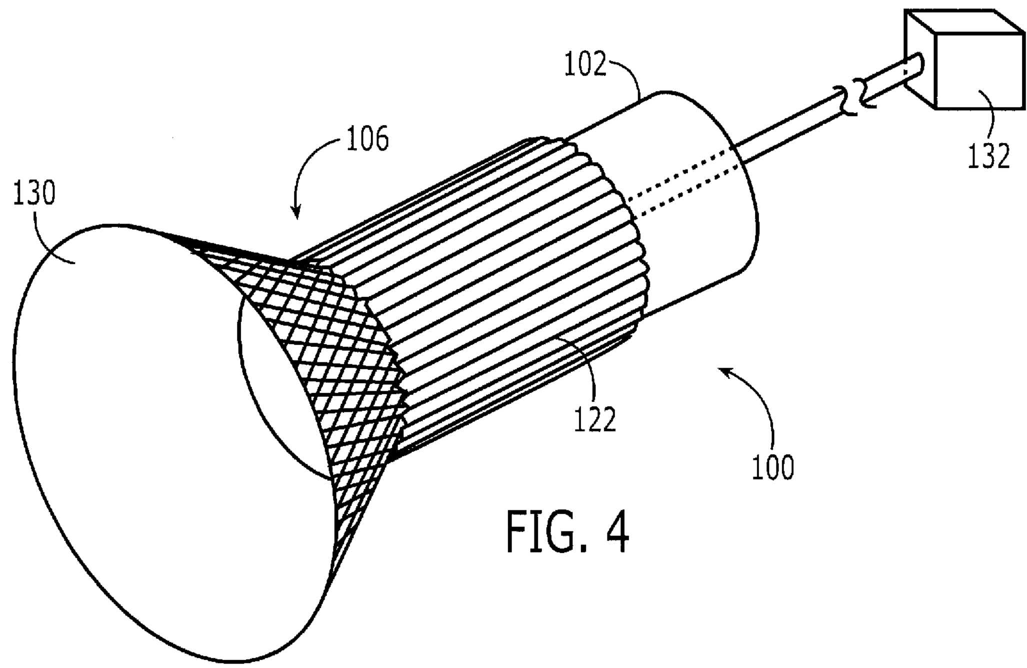
FIG. 4 is a schematic drawing showing an area illuminated by a light of the device shown in FIG. 1.

FIGS. 3 and 4 shows a distal end 106 of the probe 100 including a lighting element formed as an array 124 of optical fibers 122 with distal ends of the optical fibers aligned to illuminate a selected area of target tissue distal of the distal end 106. The fibers 122 extend from a light source 132 through the probe 100 with the individual fibers 122 disposed around a circumference of the elongated shaft 102. Those skilled in the art will understand that the light source 132 may be either housed in a proximal portion of the probe 100 or external to the probe 100 with the fibers 122 extending to a connector formed in the proximal portion of the probe 100 for coupling to fibers extending to the light source 132. Alternatively, as would be understood by those skilled in the art, a light source including, for example, one or more LED's may be located in the distal end of the probe 100 with a movable filter changing the frequency of the output light from white to the selected range of approximately 440 nm. As would be understood by those skilled in the art, either the illuminating light or the reflected light may be filtered to select a desired frequency range and, although LED's are discussed as an exemplary light source, any suitable light source may be employed. A protective cover 128 may be included to serve as a protective jacket around the optical fibers 122, to prevent damage as the probe 100 is advanced through a laparoscope, endoscope etc. The electrical conductor 110 powering the ultrasound crystal 108 may extend radially within or radially outside the fiber array 124 or the leads of the conductor 110 may be interspersed between the fibers 122 at substantially the same distance from the longitudinal axis of the probe 100.

FIG. 4 shows an exemplary cone of light 130 emitted from the array of optic fibers 122. The light provided may be, for example, at a frequency of about 440 nm (blue light), which has been shown to facilitate the visual identification of endometriosis lesions. As would be understood, the output energy of the light source (or sources) 132 is selected to provide a desired illumination of the target tissue without unduly heating the illuminated tissue. As described above, the light source 132 may be located in the handle of the probe 100 or may be external to the device. It will be understood by those of skill in the art that a source of white light may also be connected to the optic fibers 122. Alternatively, as would be understood by those skilled in the art, a single source of light may be controlled (e.g., through the use of one or more movable filters) to provide both the white light and the wavelength selected to aid in the identification of target tissue.

The standard power amplifiers used in many hospitals are designed to work with a 50 ohm load. However, an exemplary probe 100 according to the invention will likely have an impedance considerably lower than 50 ohm. In order to prevent a significant loss of energy efficiency of the probe 100, a transformer is preferably used to match the impedance of the probe 100 to the standard 50 ohm generator. As the size of these transformers makes them unsuitable for placement in the elongated shaft 102 of the probe 100, the transformer may need to be located up to 12" or 18" from the crystal 108. Conventional wire is not well adapted to carry the required high frequency signals that distance from the transformer to the crystal 108. Thus, according to an exemplary embodiment of the probe 100, the electrical connector 110 comprises a transmission line capable of delivering the high frequency energy from the transformer to the ultrasound crystal 108. For example, the transmission line may be made of Pyralux printed circuit board clads so that the impedance of the transmission line is a function of the width of the printed conductor which may be selected to obtain the desired impedance. As would be understood by those skilled in the art, conventional radio frequency equipment is typically designed to work with standard 50 Ohm or 75 Ohm coaxial cables and load impedances. However, an exemplary probe 100 according to the invention will likely have impedance considerably lower than 50 Ohm. In order to prevent a significant emission of energy in the air and a loss efficiency of the probe 100, a transformer is preferably used to match the impedance of the probe 100 to the standard 50 ohm generator output. As the size of these transformers makes them unsuitable for placement in the elongated shaft 102 of the probe 100, the transformer may need to be located up to 18" from the crystal 108. According to an exemplary embodiment of the probe 100, the electrical conductor 110 comprises a low impedance transmission line capable of delivering the high frequency energy from the transformer to the ultrasound crystal 108. For example, the low impedance transmission line may be made of Pyralux flexible double clad printed circuit board by cutting a strip of the material so that the impedance of the transmission line is a function of the width of the strip which may be selected to obtain the desired impedance.

The physician first uses the blue light to illuminate target tissue while observing the illuminated tissue using, for example, vision tools normally incorporated into a laparoscope. As would be understood by those skilled in the art, lesion tissue is relatively easily identified when illuminated with this wavelength of light. After one or more lesions have been detected, the user places the ultrasound crystal directly on each lesion to deliver energy directly thereto to ablate the lesion. As would be understood by those skilled in the art, the energy and frequency settings for the ultrasound crystal are preferably selected to achieve a desired depth and degree of heating of the target tissue.

Although the preceding description of an exemplary embodiment focused on a device for visualizing and treating endometriosis lesions, the device may be used for other applications. For example, specific wavelengths of light may be used to detect other target tissue (e.g., sites of abnormal bleeding such as ulcerous bleeding, bladder disease lesions, bladder cancer lesions, etc.). The ultrasound probe may be then be applied to treat the identified target tissue as desired. For example, the probe may be employed to stop bleeding by coagulating blood in affected tissues.

The above exemplary embodiment of the invention provides light of at least one wavelength tailored to facilitate the visual identification of target tissue to be treated. However, the system according to the invention may also be used to automatically control and guide a therapeutic treatment in response to data provided by an imaging apparatus. For example, a feedback loop may be used to automatically detect target tissue having predefined properties. After detection, the ultrasound probe may be automatically controlled as would be understood by those skilled in the art to treat the identified target tissue. More specifically, the spectral signal of light reflected from tissue may be detected with differences in this spectral signal being detected to distinguish target tissue from non-targeted tissue. The user may input data as part of the feedback loop or the procedure may be fully automated.

Another exemplary embodiment of the present invention comprises a device that integrates the ability to provide narrow band images (NBI) in two or more bandwidths, with a therapeutic component guided in real time based on spectral data reflected from tissue. The device may preferably use NBI filters to limit the emitted light to short wavelengths, for example, in and about the blue light region and the therapeutic component of the device comprises an energy source such as an ultrasound crystal as described above or other treatment device.

The system may be used to, for example, differentiate between superficial and deep vascular lesions using the spectral signal and to provide real-time feedback to guide and adjust the therapeutic response based on the detected characteristics of the lesion. As would be understood by those skilled in the art, adjustments may be made during the procedure to any or all of the frequency at which the transducer is excited, the power delivered and/or the duration of energy delivery.

The NBI system may be applied to numerous conditions. One exemplary procedure that would benefit from NBI technology is the treatment of endometriosis, due to improvements in diagnosis as explained above. The ability to differentiate and treat multiple superficial (thin) and deep (thick) lesions in the same patient provides a significant advantage over conventional techniques. Other applications may include the treatment of interstitial cystitis, distinguishing between superficial capillaries and thick veins when viewing the gastro-intestinal mucosa, and determining a depth of invasion of esophageal cancer. Additional applications include diagnosis of Barrett's esophagus and detection of capillary blood vessels in angiogenic squamous dysplasia in high risk smokers.

The feedback loop according to embodiments of the invention may comprise an automated system linking the spectral signal received from the target tissue to the energy delivery components. Alternatively, the system may allow the user to manually change settings for power delivery based, for example, on information corresponding to the spectral signal.

Figure 5:
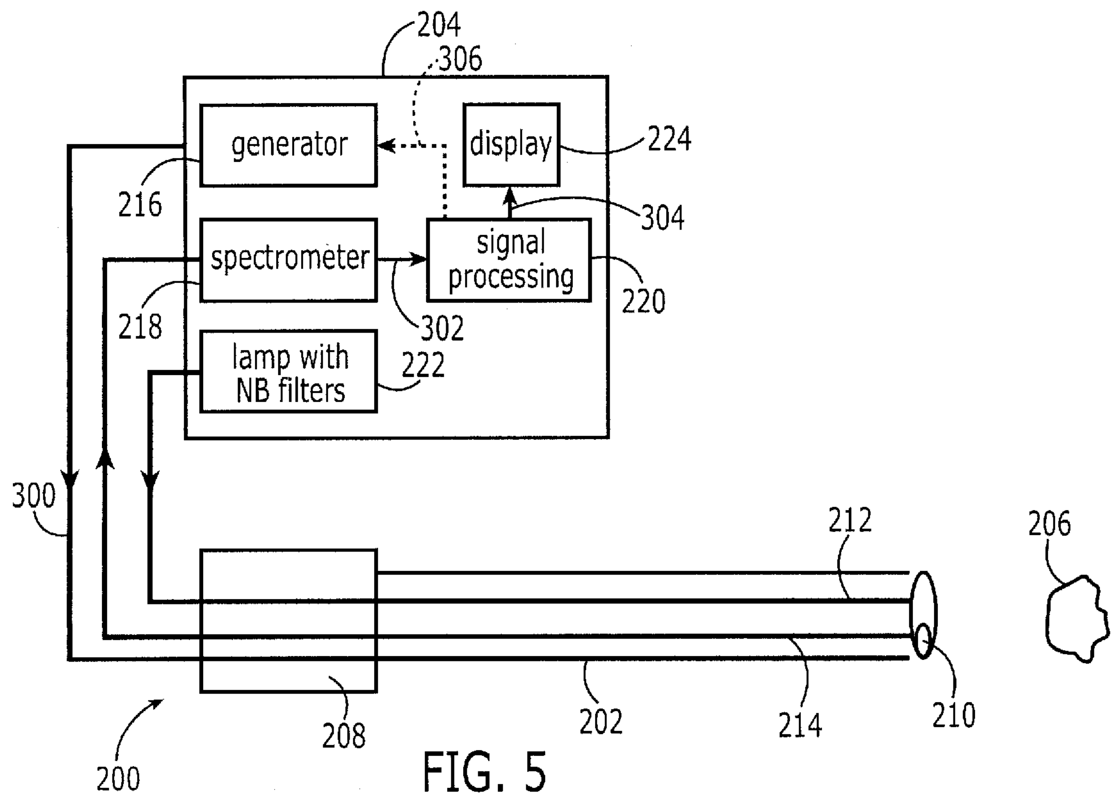
FIG. 5 is a schematic drawing showing a therapeutic device according to an embodiment of the present invention.
Figure 6:
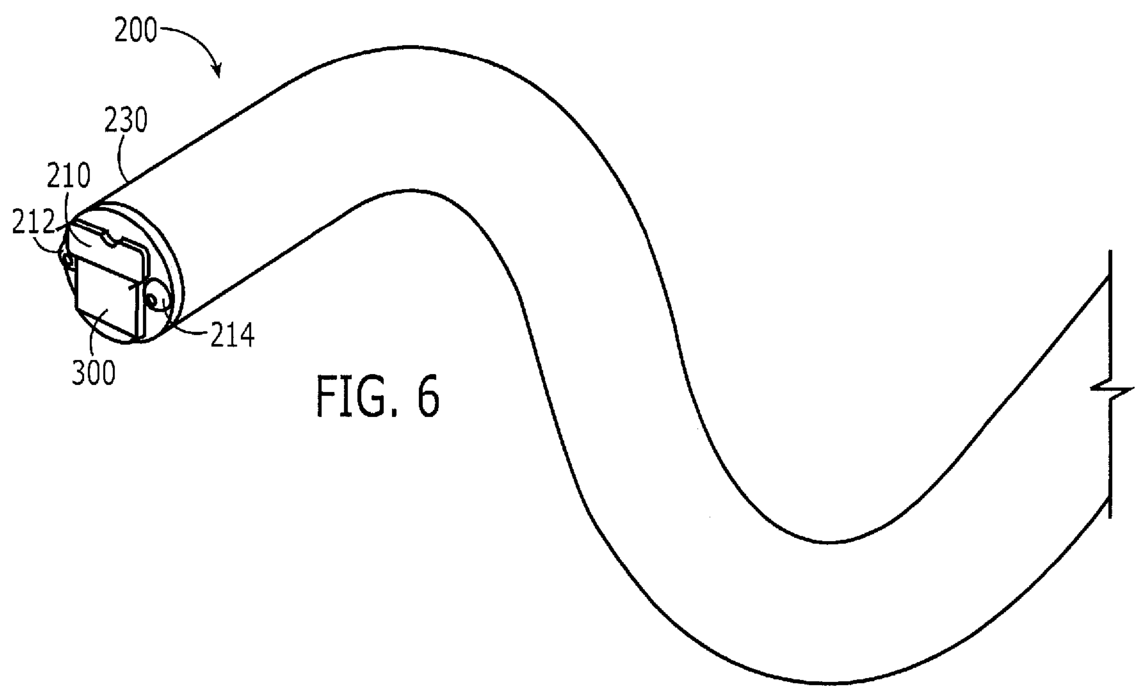
FIG. 6 is perspective view showing an elongate shaft of the therapeutic device of FIG. 1.
Figure 7:
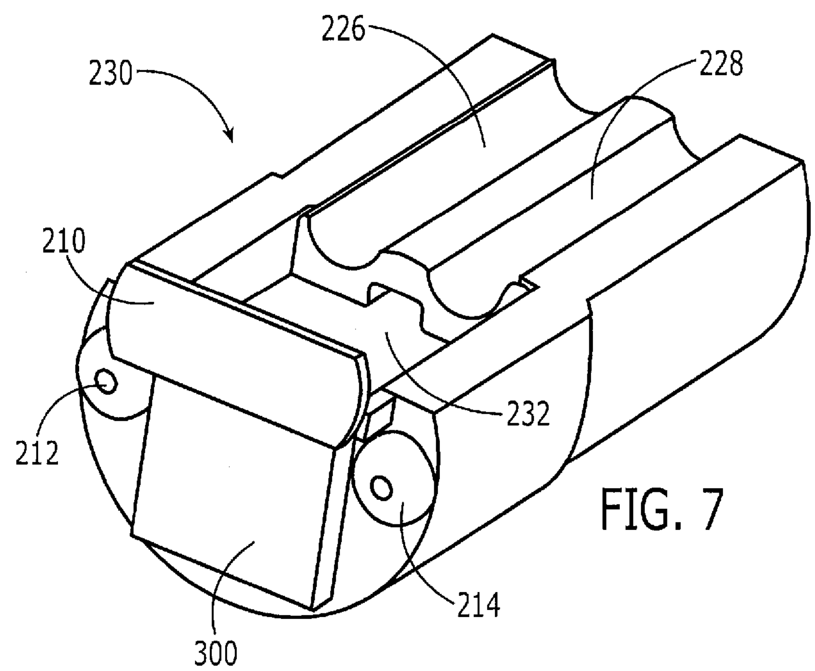
FIG. 7 is an exploded view showing a distal tip with an ultrasound crystal of the therapeutic device of FIG. 1.

An exemplary schematic of the therapeutic device according to the invention is shown in FIGS. 5-7. The device 200 according to this embodiment may have an outer diameter of approximately 10 mm so that it will fit in a 10 mm trocar. However, the device 200 may be of any desired size consistent with an intended use. The device 200 comprises an elongated shaft 202 that extends distally from a housing 208 which may preferably be shaped as a handle to be grasped during use and a control unit 204 operatively connected to the elongated shaft 202.

At least one illuminating fiber 212 and one sensing fiber 214 extend along the length of the elongated shaft 202 with the illuminating fiber 212 operatively connected to a light source such as a lamp 222 generating illumination of at least one wavelength. The illuminating fiber 212 and the sensing fiber may extend through the elongate shaft 202 such that a distal end of each of the fibers 212, 214 are exposed at a distal end 226 of the elongate shaft 202, as shown in FIG. 6. As would be understood, the light source may comprise individual sources of more than one wavelength (e.g., a source of white light and a source of blue light) or a single lamp 222 in conjunction with one or more filters allowing selected wavelengths of light to pass therethrough to the illuminating fiber 212. For example, the narrow band light may be in the blue region, with wavelengths of 400 to 430 nm and more preferably about 385 to 415 nm, 430 to 460 nm and more preferably about 415 to 445 nm and 485 to 515 nm and more preferably about 470 to 500 nm. By using narrow band filters, a large difference in penetration depth between the targeted wavelengths may be obtained.

Light reflected from the target tissue 206 returns to the control unit 204 via the sensing optic fiber 214 connected to a spectrometer or spectrophotometer 218. The spectral signal is carried from the spectrometer or spectrophotometer 218 to a signal processor 220 via connection 302 after which the signal processor 220 analyzes the signal and displays data corresponding thereto via a display 224 connected to the processor 220 via a connection 304. The processor 220 may also analyze the signal to determine properties of the tissue 206 from which the light was reflected and to derive appropriate commands for the treatment elements of the device based on this analysis. In one exemplary embodiment, the signal is simply displayed on the display 224 so that the user may adjust a generator 216 to achieve a desired therapeutic effect. Alternatively, the signal processor 220 may be operatively connected to the generator 216 via a connection 306 to control parameters of the generator 216 such as power, frequency and time to automatically achieve the desired effect.

In the exemplary embodiment, the generator 216 is operatively connected to an ultrasound crystal 210 via an electric connection or transmission line 300. The stimulation of the crystal 210 may be controlled to vary the depth of energy penetration into the tissue as a reverse function of the frequency. As would be understood by those skilled in the art, different higher harmonic frequencies (first, third, fifth . . . ) may be used to excite the crystal 210 to produce different effects. For example, a 3 MHz transducer would produce a deep thermal lesion when excited at the first harmonic (3 MHz), a shallower lesion at the third harmonic (9 MHz) and a superficial lesion at the fifth harmonic (15 MHz). Alternatively, as would be understood by those skilled in the art, superficial lesions may be treated using a relatively low frequency, tangential mode of resonance of the ultra sound crystal.

As shown in greater detail in FIG. 7, the crystal 210 may also be attached at the distal end 230 of the elongate shaft 202 via the transmission line 300. Similarly to the device 100, the crystal 210 may be cooled to prevent overheating and to prevent tissue from adhering thereto. For example, the distal end 230 of the elongate shaft 202 may include a space 232 proximal to the crystal 210, forming a cooling chamber. To maintain a temperature of the crystal 210, cooling fluids may be supplied to the space 232 via supply and return channels 226, 228, respectively, which extend through the elongate shaft 202 to a pump or similar device in the control unit 204.

Those of skill in the art will understand that, once lesions have been identified using the device and method according to the invention, any of a variety of methods of treatment may be employed as an alternative to or in addition to ultrasound energy. For example, surgical excision may be indicated in the case of a very thick lesion. It will also be understood that other wavelengths of light may be used to illuminate target tissue to aid in identifying tissue of different properties. The lower range, around 400 nm, of the visible spectrum (in the violet range) has advantages for imaging superficial vascular structures (capillaries). Frequencies approaching the edge of the green range (around 500 nm), are more appropriate for imaging thicker vascular structures deeper in tissue. Moving higher to orange/red frequencies (e.g., in a range around 600 nm), is preferably for imaging thicker veins.

The present invention has been described with reference to specific exemplary embodiments. Those skilled in the art will understand that changes may be made in details, particularly in matters of shape, size, material and arrangement of parts. For example, the invention is not limited to methods and devices for the ultrasound treatment of endometriosis. Accordingly, various modifications and changes may be made to the embodiments. The specifications and drawings are, therefore, to be regarded in an illustrative rather than a restrictive sense.

What is claimed is:

1. A device for treating tissue, comprising:

an elongate probe;

a light delivery unit supported by the elongate probe for illuminating a target area with light within a first wavelength band selected to enhance identification of target tissue;

an ultrasound crystal mounted at a tissue-contacting portion of the probe, the crystal being exposed at a distal end of the probe to directly contact the target tissue, the crystal being stimulated to generate ultrasound energy to treat the target tissue identified using the light delivery unit; and a cooling element for controlling a temperature of the ultrasound crystal, the cooling element delivering a coolant to a chamber over which the ultrasound crystal is mounted.

2. The device according to claim 1, wherein the first wavelength band is between approximately 385 to 415 nm.

3. The device according to claim 1, wherein the second wavelength band is between approximately 415 and 445 nm.

4. The device according to claim 1, wherein the second wavelength band is between approximately 470 and 500 nm.

5. The device according to claim 1, wherein the light delivery unit illuminates the target area with light within a second wavelength band selected to enhance identification of target tissue.

6. The device according to claim 1, wherein the ultrasound crystal is stimulated to emit energy in a frequency range of about 3 MHZ to about 20 MHZ.

7. The device according to claim 1, further comprising a stimulation controller controlling energy supplied to the ultrasound crystal to select a frequency of energy emitted thereby to permit selection of each of a plurality of harmonic frequencies of the ultrasound crystal.

8. The device according to claim 1, wherein the light delivery unit illuminates the target area with narrow band light with a wavelength between 400 and 500 nm.

9. The device according to claim 1, wherein the light delivery unit includes at least one optical fiber.

10. The device according to claim 9, wherein the light delivery unit includes an array of optical fibers.

11. The device according to claim 1, further comprising a power amplifier and a transformer matching an impedance of the ultrasound crystal to that of the power amplifier.

12. The device according to claim 11, further comprising a transmission line delivering energy from the power amplifier to the ultrasound crystal.

13. The device according to claim 1, further comprising an optical sensing element and a light analysis unit for analyzing spectral data of light reflected from the target tissue and supplied to the light analysis unit by the sensing optical element.

14. The device according to claim 1, further comprising a control unit coupled to the ultrasound crystal controlling energy emitted thereby.

15. The device according to claim 14, further comprising a light analysis unit analyzing spectral data of light reflected from the target tissue, wherein the control unit is coupled to the light analysis unit to control operation of the ultrasound crystal automatically based on tissue properties determined by the light analysis unit.

16. The device according to claim 15, further comprising a display outputting data corresponding to the determined tissue properties.

17. The device according to claim 13, wherein the light analysis unit includes one of a spectrometer and a spectrophotometer.

18. A tissue treatment system, comprising:

an elongate shaft with a distal end for insertion into one of a body lumen and a hollow organ;

an illumination optical fiber extending to a distal end of the elongate shaft;

a sensing optical fiber extending from the distal end;

a light source coupled to the illumination optical fiber;

a control unit selectively controlling the light source to provide one of a first and a second frequency band of light to the illumination optical fiber, the control unit comprising a light analysis unit coupled to the sensing optical fiber analyzing light received via the sensing optical fiber;

an energy delivery element at a tissue-contacting portion of the elongate shaft, the energy delivery element being exposed to directly contact target tissue; and a cooling element for controlling a temperature of the energy delivery element, the cooling element delivering a coolant to a chamber over which the energy delivery element is mounted.

19. The system according to claim 18, wherein the control unit is coupled to the energy delivery element and controls one of a frequency, intensity and duration of energy delivered to tissue thereby.

20. The system according to claim 18, wherein a first one of the narrow band filters generates light having a wavelength of between about 400 nm and about 500 nm.

21. The system according to claim 18, wherein the energy delivery element comprises an ultrasound crystal.

22. The system according to claim 18, further comprising a selector coupled to the control unit for selecting one of the first and second bands of light to provide to the illumination optical fiber.

23. The system according to claim 1, wherein the light delivery unit illuminates the target area with light within a second wavelength band selected to enhance identification of the target tissue, and wherein the light delivery unit includes a first narrow band filter for delivering light within the first wavelength band and a second narrow band filter for delivering light within the second wavelength band.

24. The system according to claim 18, further comprising a plurality of narrow band filters for providing light at one of the first frequency band and the second frequency band.

* * * * *